United States Patent [19]

Di Battista

[11] Patent Number: 4,621,110

[45] Date of Patent: Nov. 4, 1986

[54] ALKYL-SUBSTITUTED 4-METHYL-PIPERIDINE DERIVATIVES AND USE THEREOF AS STABILIZERS

[75] Inventor: Piero Di Battista, Peschiera Borromeo, Italy

[73] Assignee: Montedison S.p.A., Milan, Italy

[21] Appl. No.: 571,436

[22] Filed: Jan. 17, 1984

[30] Foreign Application Priority Data

Jan. 19, 1983 [IT] Italy ............................... 19172 A/83

[51] Int. Cl.$^4$ ...................... C08K 5/34; C07D 211/36
[52] U.S. Cl. ..................................... 524/100; 544/129; 544/212; 546/186; 546/188; 546/187; 546/216; 546/242
[58] Field of Search ............... 546/216, 242, 186, 187, 546/188; 544/129, 212; 524/100

[56] References Cited

U.S. PATENT DOCUMENTS

| | | | |
|---|---|---|---|
| 3,086,022 | 4/1963 | Meltzer et al. | 546/186 |
| 3,338,910 | 8/1967 | Kuhnis et al. | 546/216 |
| 3,438,991 | 4/1969 | Janssen | 546/216 |
| 3,462,444 | 8/1969 | Beckett et al. | 546/216 |
| 3,684,765 | 8/1972 | Matsui et al. | 546/187 |
| 4,049,647 | 9/1977 | Holt et al. | 546/216 |
| 4,191,683 | 3/1980 | Brunetti et al. | 524/100 |
| 4,440,887 | 4/1984 | Hinksken et al. | 546/242 |
| 4,450,248 | 5/1984 | Leistner et al. | 546/187 |
| 4,526,971 | 7/1985 | Disteldorf et al. | 546/186 |
| 4,528,374 | 7/1985 | Nikles | 546/186 |

FOREIGN PATENT DOCUMENTS 1052302 12/1966 United Kingdom ................ 546/186

Primary Examiner—Joseph L. Schofer
Assistant Examiner—N. Sarofim

[57] ABSTRACT

Alkyl-substituted 4-methyl-piperidine derivatives having formula:

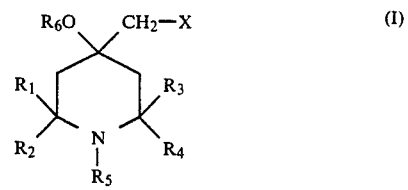

wherein X is selected from the radicals:
—N $R_{12}$ $R_{13}$;

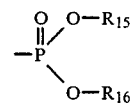

and —O—$R_{17}$

Use of the alkyl-substituted 4-methyl-piperidine derivatives of general formula (I) as stabilizers of polymeric substances and polymeric compositions stabilized with said piperidine derivatives.

31 Claims, No Drawings

ALKYL-SUBSTITUTED 4-METHYL-PIPERIDINE DERIVATIVES AND USE THEREOF AS STABILIZERS

This invention relates to new derivatives of alkyl-substituted 4-methyl-piperidine, to the use thereof as stabilizers and to the polymeric compositions stabilized with such derivatives.

BACKGROUND OF THE INVENTION

As is known, the polymeric substances are generally subject to degradation, such as discoloration and embrittlement, caused by exposure to light, especially to ultraviolet light, and by the action of oxygen and heat.

In order to prevent or delaying such degradation, it is a common technique to add to the polymeric materials various types of compounds opposing such effect, generally referred to as stabilizers.

A particular type of stabilizers which have been very successful are the sterically hindered amines (HAL) and in particular the derivatives of alkyl-substituted piperidine.

Derivatives of alkyl-substituted 4-oxy-4-methyl-piperidine are also known. Thus, e.g., from published European patent application No. 60,559 there are known polymeric products containing, as a repeating unit, alkyl-substituted 4-oxy-4-methylene piperidine, and from Belgian Pat. No. 891,835 there are known alkyl-substituted 4-oxy-4-amino-methyl-piperidines and derivatives thereof containing an alkyl-carbonyl radical or the triazine radical, bound to aminic nitrogen.

Although all these known compounds, containing the 4-oxy-methyl-piperidine radical, are excellent stabilizers for polymeric substances generally subject to deterioration, they are not fit for being utilized, with the same results, in all the polymeric substances and in all the technological uses. In fact, the known stabilizers exhibit the drawback of not possessing all the parameters and characteristics required for all technological appliances, such as low volatility, resistance to migration, thermal stability, insolubility in water, etc.

THE PRESENT INVENTION

One object of the present invention is to improve the properties of the known stabilizers containing the radical of alkyl-substituted 4-oxy-4-methyl-piperidine.

I have found that this and other objects are achieved by the derivatives of alkyl-substituted 4-methyl-piperidine having the formula:

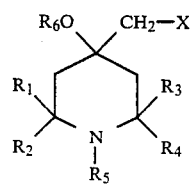

wherein:

$R_1$, $R_2$, $R_3$ and $R_4$, which may be the same or different from one another, is an alkyl radical having from 1 to 4 carbon atoms, or $R_1$ and $R_2$ and/or $R_3$ and $R_4$ together form a cyclo-alkylene radical having from 3 to 12 carbon atoms;

$R_5$ is hydrogen, an alkyl radical containing from 1 to 4 carbon atoms, an oxyalkyl radical or an alkoxy radical containing from 1 to 6 carbon atoms, an aryl or aryl-alkyl radical containing from 6 to 18 carbon atoms, an alkenyl radical containing from 2 to 6 carbon atoms, or the group

wherein $R_7$ is hydrogen, an alkyl radical containing from 1 to 4 carbon atoms, or an alkoxy radical containing from 1 to 6 carbon atoms and $R_8$ is hydrogen, an alkyl radical containing from 1 to 4 carbon atoms, or the group

wherein $R_9$ is hydrogen, an alkyl radical containing from 1 to 18 carbon atoms, a phenyl or benzyl radical, or the group

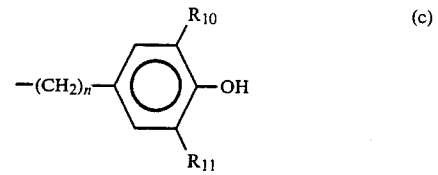

wherein n is an integer from 1 to 10, and $R_{10}$ and $R_{11}$ is hydrogen or an alkyl radical containing from 1 to 4 carbon atoms;

$R_6$ is hydrogen, an alkyl radical, an alkyl-carbonyl radical in which the alkyl group contains from 1 to 22 carbon atoms, a phenyl-alkyl-carbonyl radical, a cyclo-alkyl-carbonyl radical or a phenyl-carbonyl radical, in which the phenyl or cyclo-alkyl nucleus may be optionally substituted by alkyl groups containing from 1 to 3 carbon atoms; and X may be:

(A) —$NR_{12}R_{13}$, in which $R_{12}$ and $R_{13}$, which may be the same or different from each other, is:
 an alkyl radical containing from 1 to 10 carbon atoms;
 an alkenyl or alkynyl radical containing from 2 to 10 carbon atoms;
 benzyl, phenyl or the corresponding alkyl-substituted compounds;
 the radical:

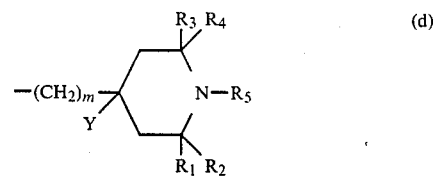

$R_{12}$ is an alkyl radical containing from 1 to 4 carbon atoms and $R_{13}$ is the radical

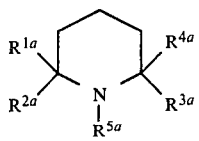
(da)

in which $R^{1a}$ to $R^{5a}$ inclusive have the same meanings as $R^1$ to $R^5$ inclusive in formula I;
wherein:
$R_1$, $R_2$, $R_3$, $R_4$ and $R_5$ have the meaning indicated hereinabove, m is an integer ranging from 0 to 3 and Y is hydrogen, a hydroxyl group, an oxy-alkyl-carbonyl radical, an oxy-phenyl-carbonyl radical, an oxy-cyclo-alkyl-carbonyl radical, in which the phenyl or cyclo-alkyl group may be alkyl-substituted;
the radical:

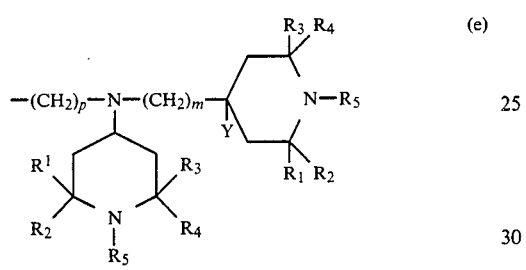
(e)

in which:
$R_1$, $R_2$, $R_3$, $R_4$, $R_5$, m and Y have the meaning indicated hereinbefore and p is an integer from 1 to 12;
the radical:

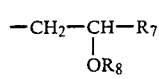
(f)

wherein: $R_7$ and $R_8$ have the values indicated hereinbefore;
$R_{12}$ and $R_{13}$ form, along with the nitrogen atom to which they are bound, a morpholine or piperidine group unsubstituted or alkyl-substituted;
$R_{12}$ and $R_{13}$ together form the group:

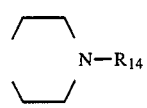
(g)

unsubstituted or alkyl-substituted in the nucleus, in which $R_{14}$ may be hydrogen, an alkyl radical containing from 1 to 6 carbon atoms, or the radical:

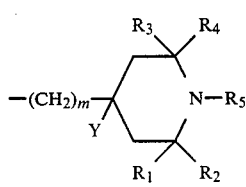
(h)

wherein m, $R_1$, $R_2$, $R_3$, $R_4$, and Y have the meaning reported hereinabove;
the triazine radical:

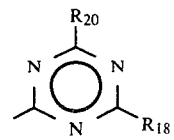
(i)

wherein $R_{20}$ and $R_{18}$, which may be the same or different, are an alkyl radical containing from 1 to 18 carbon atoms, an alkoxy or alkyl-oxy radical containing from 1 to 18 carbon atoms, or the radical

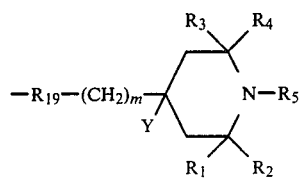

wherein: $R_1$, $R_2$, $R_3$, $R_4$, $R_5$, m and Y have the same meanings as indicated hereinbefore, and $R_{19}$ may be oxygen or —N—$R_{12}$; or
$R_{12}$ or $R_{13}$ may be hydrogen, with the prevision that, when radical (i) is present, $R_{12}$ and $R_{13}$ are not hydrogen;
(B)

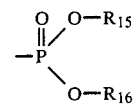

in which $R_{15}$ and $R_{16}$, which may be the same or different from each other, are hydrogen, an alkyl radical containing from 1 to 6 carbon atoms, or the group

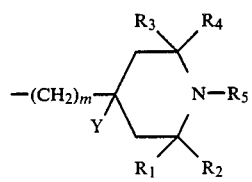
(m)

in which $R_1$, $R_2$, $R_3$, $R_4$, $R_5$, Y and m have the same meanings indicated hereinbefore; or
(C) —O—$R_{17}$, in which $R_{17}$ may be:
hydrogen;
an alkyl, alkenyl or alkynyl radical, each of them containing from 1 to 18 carbon atoms;
a benzyl, phenyl radical, optionally alkyl-substituted in the nucleus;
the radical

(b)

in which $R_9$ has the meaning indicated hereinbefore; or
the triazine radical

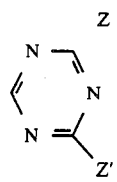

in which: Z and Z', which may be the same or different, are hydrogen, an alkyl radical containing from 1 to 18 carbon atoms, an alkoxy or alkylamino in which the alkyl radical contains from 1 to 18 carbon atoms, or the radical

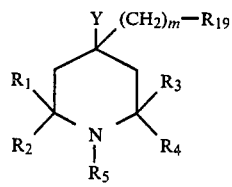

in which $R_1$, $R_2$, $R_3$, $R_4$, $R_5$, $R_{19}$, Y and m have the meanings indicated hereinabove.

All the alkyl, alkenyl or alkynyl groups containing 3 carbon atoms or more, may have a linear or ramified chain.

The present invention provides too, compositions based on synthetic polymers, stabilized to oxidation and to ageing, containing, as a stabilizer, an alkyl-substituted-4-methyl-piperidine having formula (I) in an amount sufficient to prevent any degradation of the polymer.

In the embodiment of the present invention the preferred derivatives of alkyl-substituted 4-methyl-piperidine having formula (I) are those in which:

$R_1$, $R_2$, $R_3$ and $R_4$ are methyl or ethyl radicals;

$R_5$ is hydrogen or a methyl, allyl or alkyl-ester radical;

$R_6$ is hydrogen, or a methyl or ethyl radical;

X may be selected from amongst dialkyl-amines, alkyl-piperidyl-amines, alkyl-substituted-di-piperidyl alkylene-diamines, alkyl-substituted piperazines, dioxyamino triazines, trioxy-triazines, oxy-alkyl esters, phosphonyl esters.

Examples of alkyl-substituted 4-methyl-piperidine-derivatives having formula (I), according to the present invention, are:

A. among the compounds in which $X=NH_{12}R_{13}$:

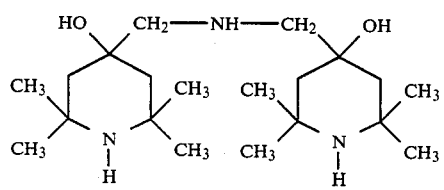

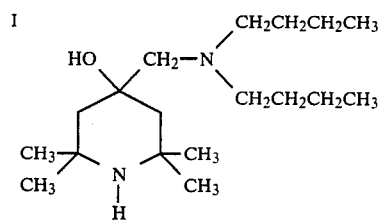

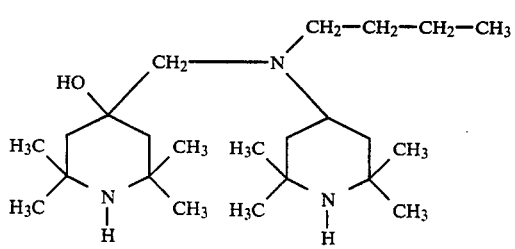

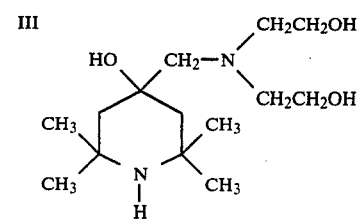

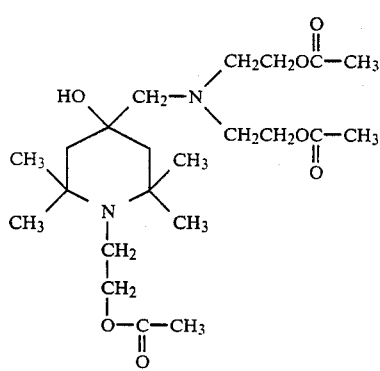

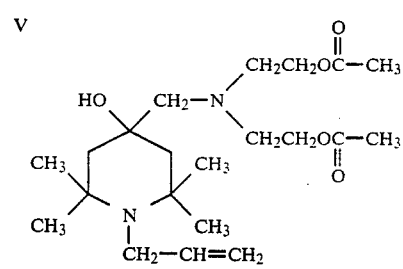

-continued
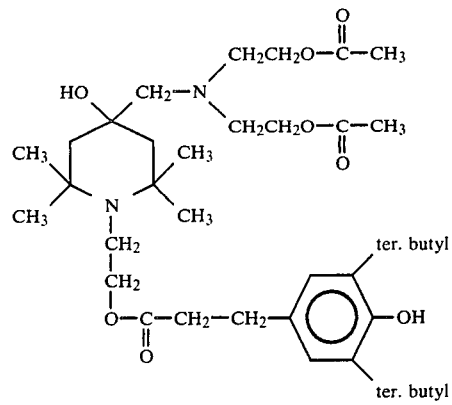
VII
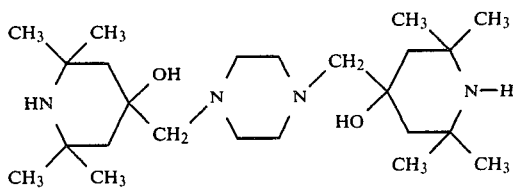
VIII
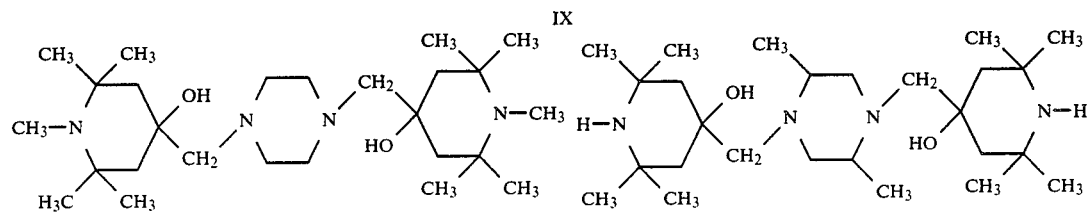
IX     X
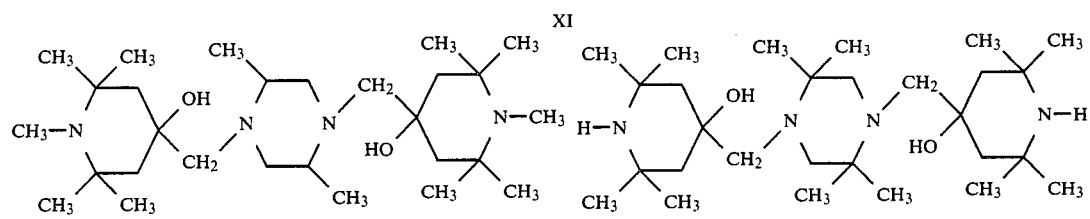
XI     XII
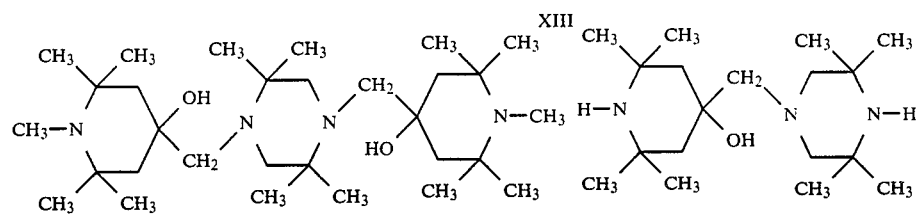
XIII     XIV
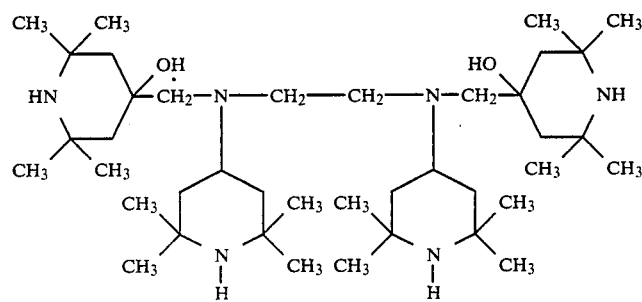
XV
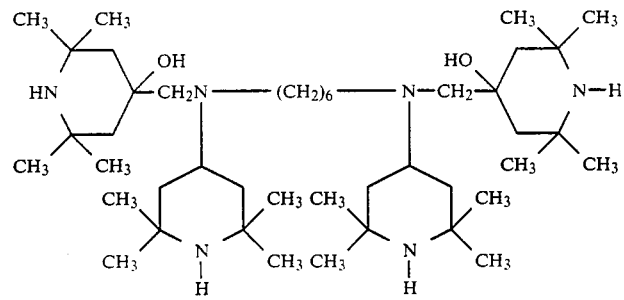
XVI -continued
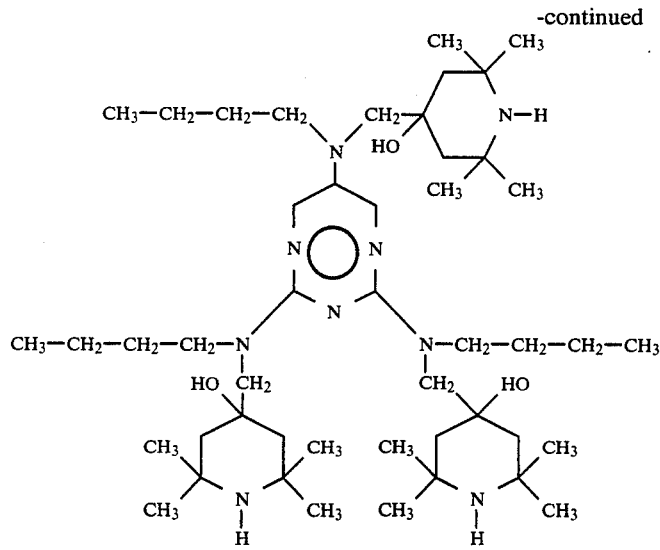
XVII
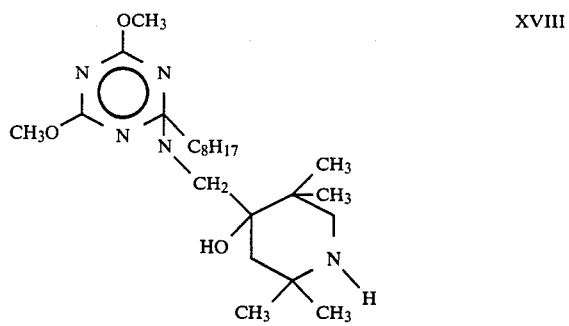
XVIII
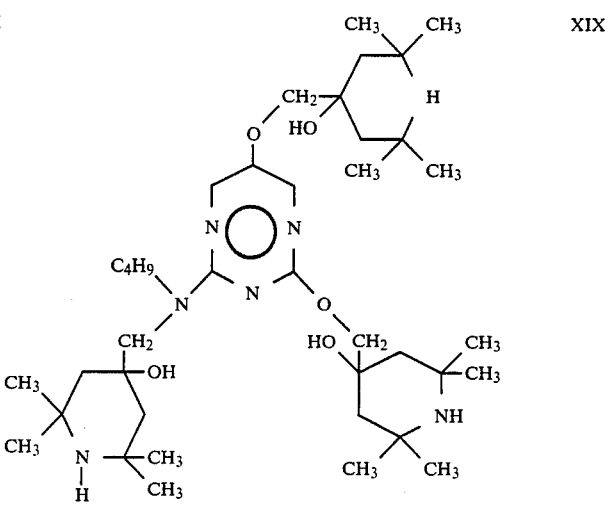
XIX
B. Among the compounds wherein
$$X = P \begin{matrix} \parallel \\ O \end{matrix} \begin{matrix} O-R_{15} \\ O-R_{16} \end{matrix}:$$
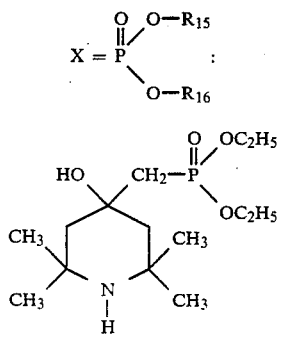
XX
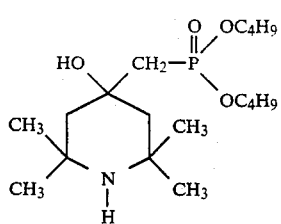
XXI
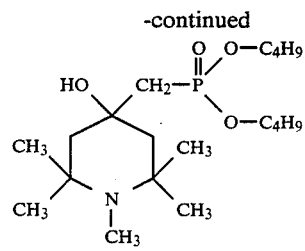
XXII
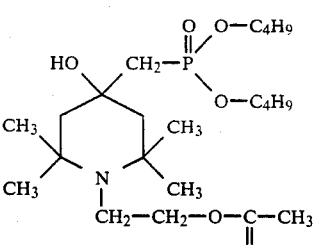
XXIII
C. Among the compounds wherein $X=O-R_{17}$:

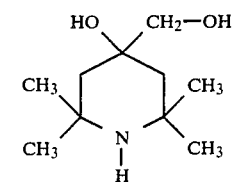
XXIV

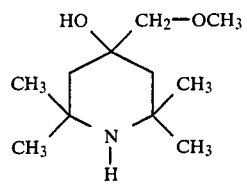
XXV

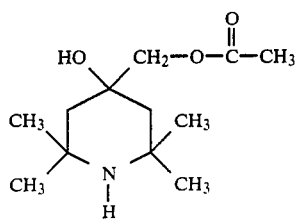
XXVI

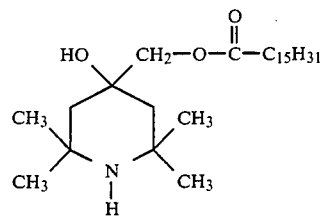
XXVII

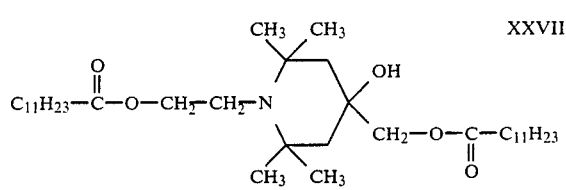
XXVIII

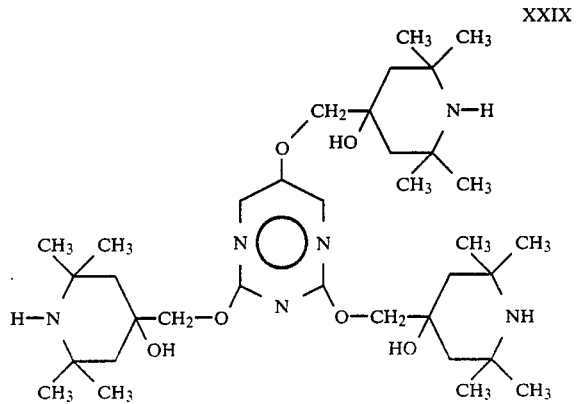
XXIX

The alkyl-substituted 4-methyl-piperidine derivatives of formula (I) may be synthesized starting from alkyl-piperidyl-4-spiro-oxirane or a derivative thereof. In particular, the compounds having formula (I) in which "X" is $-NR_{12}R_{13}$ are synthesized by reacting, in an equimolar amount, preferably in the presence of an inert organic solvent and at a temperature ranging from room temperature to 200° C., an alkyl-piperidyl-4-spiro-oxirane or a derivative thereof with a primary or secondary amine. Suitable organic solvents may be alcohols, ethers, halogen hydrocarbons, etc. Methyl alcohol is preferred. Also water can be employed as a solvent.

The compounds having formula (I) in which:

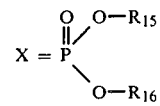

may be synthesized by reacting, in equimolar amounts, preferably in the presence of an inert solvent and at a temperature ranging from room temperature to 200° C., an alkyl-piperidyl-4-spiro-oxirane or a derivative thereof with a phosphite. Suitable solvents may be water, alcohols, ethers, halogenated hydrocarbons, etc. It is furthermore preferred to carry out the reaction in the presence of organic bases such as pyridine, triethylamine, alcoholates of alkaline metals or of alkaline-earth metals, hydrides or amides of alkaline or alkaline-earth metals, or generally substances containing quaternary ammonium halides. The amount of these organic bases in the reaction medium ranges from little catalytic amounts, such as 0.001%, up to above the stoichiometric amounts.

The compounds of formula (I) in which X is $-O-R_{17}$ may be synthesized by reacting, in equimolar amounts, preferably in the presence of an insert organic solvent and at a temperature ranging from room temperature to 200° C., an alkyl-piperidyl-4-spiro-oxirane or a derivative thereof with an alcoholate of an alkaline or alkaline-earth metal. Suitable inert organic solvents may be ethers, hydrocarbons, halogenated hydrocarbons, aromatic hydrocarbons such as xylene, toluene, etc. At the end of the reaction, a washing with water is carried out and the reaction product is recovered by evaporating the organic solvent.

The compounds of formula (I) in which X is $O-R_{17}$ and $R_{17}$ is the above reported radical

or the triazine radical, may be prepared by reacting the compound of formula XXIV with an halogen-derivative containing an acyl- or triazinyl radical, in the presence of a base such as an hydroxide or carbonate of an alkaline metal and optionally of an inert solvent, at a temperature from room temperature to 200° C.

The alkyl-substituted 4-methyl-piperidine derivatives of formula (I) of the present invention, besides possessing the well-known photostabilizing properties of the HALS, exhibit a surprising improved stabilizing action to thermo-oxidation, accompanied by a substantial water-insolubility, non-volatily and a high stability to heat.

Examples of materials which can be stabilized by the derivatives of the invention are mainly the synthetic organic polymeric substances, including:

polyolefines, such as homopolymers of olefines, among which high density and low density polyethylene, polypropylene, polystyrene, polybutene, polyisoprene and the like; the copolymers of olefines with other ethylenically unsaturated monomers such as ethylene-propylene copolymers, ethylene-butene copolymers, styrene-butadiene and styrene-acrylonitrile copolymers; the terpolymers of ethylene, propylene and a diene such as acrylonitrile-styrene-butadiene etc., and the mixtures of the above-mentioned polymers and co-polymers;

vinyl polymers containing halogen, such as polyvinyl chloride and polyvinylidene chloride, polyvinyl fluoride, chlorinated rubbers, the copolymers of vinyl chloride and of vinylidene chloride with each other or each with vinyl acetate or other ethylenically unsaturated monomers;

polymers derived from $\alpha,\beta$ unsaturated acids or derivatives thereof, such as polyacrylates, polymethacrylates, polyacrylamides, polyacrylonitrile and also the copolymers thereof;

polyacetals such as polyoxymethylene and polyoxyethylene;

polyesters such as polyethylene-terephthalates;

polyamides such as nylon 6, nylon 6-6 and nylon 6-10; and the corresponding co-polyamides;

polyurethanes and polyureas;

polymers derived from unsaturated alcohols and from unsaturated amines;

polycarbonates;

monomers and copolymers derived from epoxides such as polyethylene-oxides;

thermoplastic elastomers;

natural and synthetic rubbers, etc.

Such synthetic polymers may be employed either as powder or granules, or as shaped articles, e.g. fibres, films, sheets, foils, etc., or as latex and foams.

Of the synthetic polymers cited hereinabove, the ones which are more suited to be stabilized, according to the present invention, are the polyolefines deriving from monomers having the general formula: R—CH=CH$_2$, wherein R is an alkyl or aryl group, or a hydrogen atom.

Of the polyolefines, it is preferable to use polypropylene prevailingly consisting of isotactic macromolecules and obtained by stereospecific polymerization of propylene.

The amount of alkyl-substituted 4-methyl-piperidine derivative having formula (I) to be added to the substance to be stabilized, according to this invention, is not critical and may vary over a wide range as a function of the type, properties and particular uses of the substance. Generally, said stabilizers can be added in amounts ranging from 0.01 to 5.0% by weight.

Practically, however, the amount varies as a function of the type of substance to be stabilized. Thus, for example, in the case of the polyolefines, such amount varies from 0.01 to 2% by weight; for the halogen-containing vinyl polymers, such amount may range from 0.01 to 1% by weight; and for the polyurethanes, the polyamides and the polymers derived from $\alpha,\beta$, unsaturated acids, the amount may vary from 0.01 to 5% by weight. The derivatives of the alkyl-substituted 4-methyl-piperidines having formula (I) may be employed either alone or in admixture with other known additives such as antioxidants, UV-ray absorbers, pigments, fillers, basic nitrogen containing polycondensates, stabilizers, etc.

Examples of such additives are oxo-benzo-triazoles, oxo-benzo-phenones, Ni-stabilizers, metal soaps, phenolic antioxidants, phosphites, phosphinites, thioesters, hydroquinone derivatives, triazinic compounds, acylamino-phenols, benzylphosphonates, sterically hindered phenols such as 4,4'-bis-butylidene-bis-(2,6-di-ter.butyl)-phenol; triazino-phenol compounds, etc.

Such additives can be utilized along with the compounds having formula (I) in a weight ratio in the range of from 0.5:1 to 3:1.

The incorporation of the compounds having formula (I) or of the mixture containing said compounds into the synthetic polymer may be accomplished according to any known procedure and in any step, before or after polymerization, or during the manufacture of the shaped article from said polymer.

Thus, for example, the powdered additives may be merely mixed, under stirring, to the polymer; or the polymer may be mixed with a solution of the stabilizers in a proper solvent, which is then evaporated; or the stabilizers can be added to the polymer at the end of the polymerization.

Furthermore, the compounds having formula (I) can be also added to the substance to be stabilized in the form of a master batch containing these compounds at a concentration ranging, for example, from 2.5 to 50% by weight.

It is furthermore possible to attain the stabilizing effect by applicating the stabilizer onto the manufactured article, for example by immerging it into a stabilizer solution or dispersion and by successively evaporating the solvent or the dispersant, or by dissolving the stabilizer in a suitable solvent and spraying the solution onto the manufactured article's surface.

The following non-limitative example are given for a more detailed understanding of the present invention and for further enabling those skilled in the art to practice the same.

In the examples, unless otherwise specified, all the parts are to be considered as parts by weight.

EXAMPLE 1

16.9 g (0.1 moles) of 2,2,6,6-tetra-methyl-4-spiro-oxirane and 21.2 g (0.1 moles) of 2,2,6,6-tetra-methyl-4-n.-butyl-amino-piperidine were dissolved in 100 cc of methyl alcohol and heated, in a closed tube, at 150° C. for 6 hours.

The tube was opened, the solvent was removed by evaporation, and the product obtained was distilled under vacuum at 150° C. and 0.00053 da N/cm$^2$ of residual pressure.

On the basis of the I.R. and N.M.R. spectra and to the centesimal analyses, formula III indicated on page 9 of the present application was attributed to the product.

EXAMPLES 2 TO 11

The reaction was conducted under the same conditions of examples 1. The reagents, the reaction temperature and time, the obtained compound and its melting point are recorded on the following Table I.

Column 6 (obtained compound No.) refers to the list of compounds indicated on pages 9 to 14 of the present application.

TABLE I

| Ex. No. | REAGENTS | | Reaction time in h | Reaction temper. in °C. | Compound obtained No. | Appearance | Melting point in °C. |
|---|---|---|---|---|---|---|---|
| 2 | ![1,4-dioxa-spiro piperidine with 2,2,6,6-tetramethyl, NH] | NH₃ | 5 | 150 | I | white solid | 113–115 |
| 3 | " | HN(CH₂CH₂OH)₂ | 8 | 150 | IV | " | 105–107 |
| 4 | " | piperazine (HN–NH) | 11 | 100 | VIII | " | 185–186 |
| 5 | " | 2,5-dimethylpiperazine | 8 | 120 | X | " | 181–183 |
| 6 | " | 2,2,5,5-tetramethylpiperazine | 10 | 140 | XII | " | 218–220 |
| 7 | " | HN—(CH₂)₂—NH bis(2,2,6,6-tetramethylpiperidin-4-yl) | 11 | 150 | XV | " | 178–180 |
| 8 | " | HN—(CH₂)₆NH bis(2,2,6,6-tetramethylpiperidin-4-yl) | 19 | 150 | XVI | " | 126–128 |
| 9 | N-methyl-2,2,6,6-tetramethyl-piperidine spiro epoxide | piperazine (HN–NH) | 10 | 100 | IX | " | 152–153 |

TABLE I-continued

| Ex. No. | REAGENTS | Reaction time in h | Reaction temper. in °C. | Compound obtained No. | Appearance | Melting point in °C. |
|---|---|---|---|---|---|---|
| 10 | " 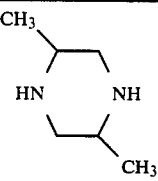 | 8 | 120 | XI | " | 212–214 |
| 11 | " 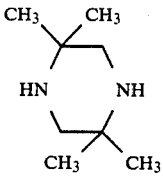 | 10 | 150 | XIII | " | 217–219 |

EXAMPLE 12

16.9 g (0.1 mole) of 2,2,6,6-tetra-methyl-piperidyl-4-spiro-oxirane and 15 g (0.1 mole) of diethyl-phosphite were dissolved in 80 cc of anhydrous ethyl alcohol.

11.7 g of triethylamine were added to the mixture which was introduced into a tube. After having closed the end of the tube, the mixture was heated at 120° C. for 10 hours. The tube was opened, and the solvent, the triethyl-amine and the small amounts of unreacted reagents, were removed under vacuum.

An oily, light-yellow product was obtained, to which, on the basis of the I.R. and N.M.R. spectra and of the centesimal analyses, formula XX, shown on page 14 of this application, was attributed.

EXAMPLE 13

16.9 g (0.1 mole) of 2,2,6,6-tetra-methyl-piperidyl-4-spiro-oxirane were dissolved in 50 cc of an aqueous solution at 50% by weight of $H_2SO_4$.

The solution was allowed to stand overnight, whereupon NaOH up to a pH=11 was added thereto, and the reaction product was extracted with $CHCl_3$. After removal of the organic solvent, a white solid product having a melting point of 130° C.–132° C. was obtained. On the basis of the I.R. and N.M.R. spectra and of the centesimal analyses, formula XXIV indicated on page 15 of the present application was attributed to the product.

EXAMPLE 14

16.9 g of 2,2,6,6-tetramethyl-piperidyl-4-spiro-oxirane and 5.5 g of sodium methylate were dissolved in 80 cc of methanol and heated in a tube closed at its end during 10 hours at 120° C. After evaporation of the solvent, a yellow oil was obtained,, which, as revealed by the I.R. and N.M.R. spectra and by the centisimal analyses, was corresponding to compound XXV indicated on page 15 of the present application.

EXAMPLE 15

16.9 g of 2,2,6,6-tetramethyl-piperidyl-4-spiro-oxirane were dissolved in 40 cc of glacial acetic acid.

The solution was introduced into a tube, which was closed at its both ends, and was heated to 120° C. during 8 hours.

After neutralization with NaOH, the reaction product was distilled at 120° C. and at 0.0026 da $N/cm^2$.

On the basis of the I.R. and N.M.R. spectra and of the centesimal analyses, the product was attributed formula XXVI indicated on page 16 of the present application.

EXAMPLE 16

18.7 g of the product obtained in example 13 and having formula XXIV, and 28.4 g of ethyl palmitate were molten at 160°–170° C. in the presence of small traces of LiOH. After removal of the ethyl alcohol formed during the reaction, the reaction product was diluted with $CH_2Cl_2$. The resulting organic solution was repeatedly washed with water up to neutrality, and the solvent was evaporated. The dried product was in the form of a light yellow oil.

On the basis of the I.R. and N.M.R. spectra and of the centesimal analyses, the product was attributed formula XXVII reported on page 16 of the present application.

EXAMPLE 17

The following procedure was followed in order to prove the stabilizing properties of the new compounds.

200 cc of a chloroform solution containing the stabilizing compounds to be tested, in the amount indicated in Table II, were added to 300 g of non-stabilized polypropylene having an inherent viscosity, determined in tetraline at 130° C., of 162 cc/g, a residue to the extraction with heptane of 96.5% and an ash content of 80 ppm.

The mixture was stirred for about 6 hours, at room temperature, in a rotary evaporator, then it was dried at $0.133 \cdot 10^{-4}$ da $N/cm^2$ and at 50° C. for 1 hour. The resulting additioned powder was extruded in a Brabender extruder at 220° C. and granulated. The granules were transformed into films having a uniform thickness of 50–60 microns, and to small plates having a thickness of 1 mm.

On the manufactured articles so obtained, the thermo-oxidative stability and the photo-oxidative stability were determined.

The thermo-oxidative stability was determined on the basis of the resistance to ageing in oven, considered as the embrittlement time (E.T.) necessary to be able to observe with the naked eye, on the examined plate, surface cracks and chalkings and other modifications due to exposure in oven at 150° C. with air circulation.

The photo-oxidative stability was determined on the basis of the embrittlement time (E.T.) considered as the time necessary to obtain the rupture of the film by means of only one bending at 180° C., after exposure to Xenotest 1200 (manufactured by Hanau) under conditions conforming to standard DIN 54004:
 temperature of the back panel: 43±2° C.
 relative humidity: 50±5%
 alternate exposure
 irradiation with light having a wave length above 300 m.

TABLE II

| Example No. | STABILIZER Compound No. | Amount in % by weight | Thermo-oxid. stability E.T. in hours | Photo-oxid. stability E.T. in hours |
|---|---|---|---|---|
| — | — | — | <24 | 100 |
| 1 | III | 0,5 | 100 | 3,400 |
| 4 | VIII | 0,5 | 200 | 2,900 |
| 6 | XII | 0,5 | 200 | 3,800 |
| 7 | XV | 0,3 | 330 | 2,800 |
| 7 | XV | 0,5 | 500 | 4,200 |
| 8 | XVI | 0,3 | 330 | 2,700 |
| 8 | XVI | 0,5 | 500 | 4,300 |
| 12 | XX | 0,5 | 170 | 3,000 |
| 16 | XXVII | 0,5 | 100 | 3,100 |

I claim:
1. Alkyl-substituted 4-methyl-piperidine derivatives having formula:

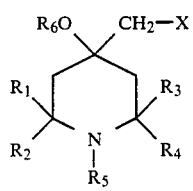

(I)

wherein:
$R_1$, $R_2$, $R_3$ and $R_4$, which may be the same or different, is an alkyl radical having from 1 to 4 carbon atoms, or $R_1$ and $R_2$ and/or $R_3$ and $R_4$ together form a cyclo-alkylene radical having from 3 to 12 carbon atoms;
$R_5$ is hydrogen, an alkyl radical containing from 1 to 4 carbon atoms, an oxyalkyl or alkoxy radical containing from 1 to 6 carbon atoms, an aryl or aryl-alkyl radical containing from 6 to 18 carbon atoms, an alkenyl radical having from 2 to 6 carbon atoms, or the group:

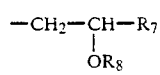

(a)

wherein $R_7$ is hydrogen, an alkyl radical containing from 1 to 4 carbon atoms or an alkoxy radical containing from 1 to 6 carbon atoms, and $R_8$ is hydrogen, an alkyl radical containing from 1 to 4 carbon atoms, or the group:

(b)

wherein $R_9$ is hydrogen, an alkyl radical containing from 1 to 18 carbon atoms, a phenyl or benzyl radical or the group:

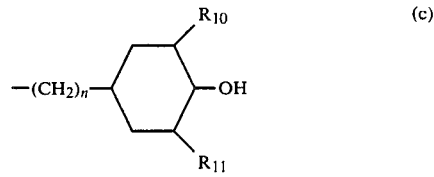

(c)

wherein n is an integer from 1 to 10, and $R_{10}$ and $R_{11}$ is hydrogen or an alkyl radical containing from 1 to 4 carbon atoms;
$R_6$ is hydrogen, an alkyl radical, an alkyl-carbonyl radical, in which the alkyl group contains from 1 to 22 carbon atoms, a phenyl-alkyl-carbonyl radical, a cyclo-alkyl-carbonyl radical or a phenyl-carbonyl radical, in which the phenyl or cyclo-alkyl nucleus is optionally substituted by alkyl groups containing from 1 to 3 carbon atoms; and
X may be:
(A) —$NR_{12}R_{13}$, in which $R_{12}$ and $R_{13}$, which may be the same or different from each other, is:
 an alkyl radical containing from 1 to 10 carbon atoms;
 an alkenyl or alkynyl radical containing from 2 to 10 carbon atoms;
 benzyl, phenyl or the corresponding alkyl-substituted compounds;
the radical:

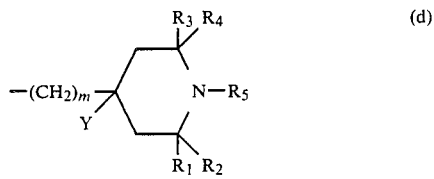

(d)

wherein:
$R_1$, $R_2$, $R_3$, $R_4$ and $R_5$ have the meaning indicated hereinbefore, m is 0 or an integer from 1 to 3 and Y is hydrogen, a hydroxyl group, an oxyalkyl-carbonyl radical, an oxy-phenyl-carbonyl-radical, an oxy-cyclo-alkyl-carbonyl radical, in which the phenyl or cyclo-alkyl group may be alkyl-substituted;
the radical:

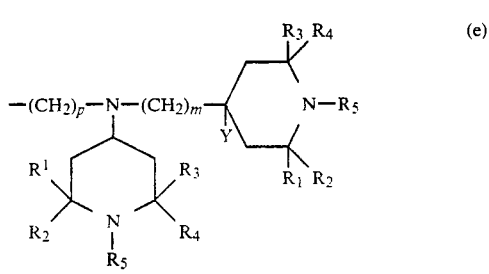

(e)

wherein:
$R_1$, $R_2$, $R_3$, $R_4$, $R_5$, m and Y have the same meaning explained hereinbefore and p is an integer ranging from 1 to 12;
the radical

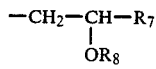 (f)

wherein: $R_7$ and $R_8$ have the values indicated hereinabove;

$R_{12}$ and $R_{13}$ form, along with the nitrogen atom they are linked to, an unsubstituted or alkyl-substituted morpholine or piperidine group;

$R_{12}$ and $R_{13}$ together form the group:

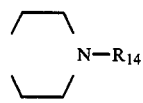 (g)

unsubstituted or alkyl-substituted in the nucleus, in which $R_{14}$ is hydrogen, an alkyl radical containing from 1 to 6 carbon atoms, or the radical:

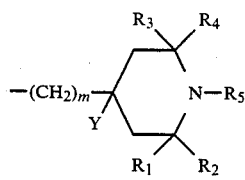 (h)

wherein m, $R_1$, $R_2$, $R_3$, $R_4$ and Y have the meaning indicated hereinbefore;

the triazine radical

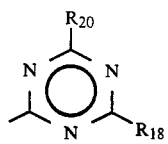 (i)

wherein $R_{20}$ and $R_{18}$, which may be the same or different, each is an alkyl radical containing from 1 to 18 carbon atoms, an alkoxy or alkyloxy radical containing from 1 to 18 carbon atoms, or the radical:

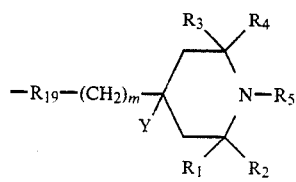

wherein: $R_1$, $R_2$, $R_3$, $R_4$, $R_5$, m and Y have the meanings indicated hereinbefore and $R_{19}$ may be oxygen or $-N-R_{12}$; or $R_{12}$ and $R_{13}$ may be hydrogen, with the prevision that, when radical (i) is present $R_{12}$ and $R_{13}$ are not hydrogen;

(B)

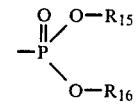

in which $R_{15}$ and $R_{16}$, which may be the same or different from each other, each is hydrogen, an alkyl radical containing from 1 to 6 carbon atoms, or the group:

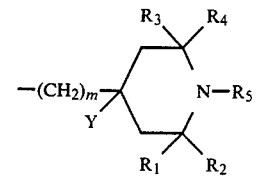

in which $R_1$, $R_2$, $R_3$, $R_4$, $R_5$, Y and m have the same meaning indicated hereinbefore; or (C) $-O-R_{17}$, in which $R_{17}$ may be:
hydrogen;
an alkyl, alkenyl or alkynyl radical, each containing from 1 to 18 carbon atoms;
a benzyl, phenyl radical, optionally substituted in the nucleus;
the radical:

 (b)

in which $R_9$ has the meaning indicated hereinabove; or
the triazine radical

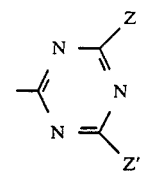 (n)

in which: Z and Z', which may be the same or different, each is hydrogen an alkyl radical containing from 1 to 18 carbon atoms, an alkoxy or alkylamino group in which the alkyl radical contains from 1 to 18 carbon atoms, or the radical:

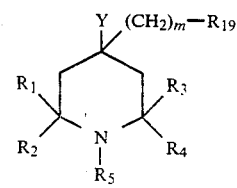

in which $R_1$, $R_2$, $R_3$, $R_4$, $R_5$, $R_{19}$, Y and m have the same meanings indicated hereinbefore.

2. Alkyl-substituted 4-methyl-piperidine derivatives according to claim 1, in which $R_1$, $R_2$, $R_3$, $R_4$ are methyl or ethyl radicals.

3. Alkyl-substituted 4-methyl-piperidine derivatives having formula (I), according to claim 1, wherein $R_5$ is hydrogen.

4. Alkyl-substituted 4-methyl-piperidine derivatives having formula (I), according to claim 1, wherein $R_5$ is methyl or allyl radical.

5. Alkyl-substituted 4-methyl-piperidine derivatives having formula (I), according to claim 1, wherein $R_5$ is an alkyl-ester radical.

6. Alkyl-substituted 4-methyl-piperidine derivatives having formula (I), according to claim 1, wherein $R_6$ is hydrogen.

7. Alkyl-substituted 4-methyl-piperidine derivatives having formula (I), according to claim 1, wherein $R_6$ is a methyl or ethyl radical.

8. Alkyl-substituted 4-methyl-piperidine derivatives having formula (I), according to claim 1, in which X is selected from the group consisting of dialkyl-amines, alkyl-piperidyl-amines, alkyl-substituted-di-piperidyl-alkylen-diamines, alkyl-substituted piperazines, dioxy-amino-triazines, trioxy-triazines, oxy-alkyl-esters and phosphinyl-esters.

9. A composition comprising a synthetic organic polymeric substance stabilized to light, to oxygen and to heat, characterized in that it contains in an amount sufficient to prevent any degrading action of the polymer, a derivative of alkyl-substituted 4-methyl-piperidine having formula (I) of claim 1.

10. A composition according to claim 9, characterized in that the derivative of alkyl-substituted 4-methyl-piperidine having general formula (I) is present in an amount ranging from 0.01 to 5% by weight referred to the synthetic organic polymeric substance.

11. A composition according to claim 9 characterized in that the synthetic polymeric substance is a polyolefine.

12. A composition according to claim 11, characterized in that the polyolefine is polypropylene prevailingly consisting of isotactic macromolecules.

13. A composition according to claim 11, characterized in that the derivative of alkyl-substituted 4-methyl-piperidine having general formula (I) is contained therein in an amount ranging from 0.01 to 2% by weight.

14. A composition according to claim 9, characterized in that the synthetic polymeric substance is a halogen-containing vinyl polymer.

15. A composition according to claim 14, characterized in that the alkyl-substituted 4-methyl-piperidine derivative having general formula (I) is contained therein in an amount ranging from 0.01 to 1% by weight in respect of the halogen-containing vinyl-polymer.

16. A composition according to claim 9, characterized in that the synthetic polymeric substance is a polyurethane, a polyamide or a polymer derived from an α,β unsaturated acid.

17. A composition according to claim 16, characterized in that the alkyl-substituted 4-methyl-piperidine derivative having general formula (I) is contained therein in an amount ranging from 0.01 to 5% by weight in respect of the polymeric substance.

18. A composition according to claim 9, characterized in that the alkyl-substituted 4-methyl-piperidine derivative having general formula (I) is employed in admixture with other additives selected from antioxidants, UV-ray absorbers, pigments, fillers, basic nitrogen containing polycondensates and stabilizers.

19. A composition according to claim 18, characterized in that the other additives are employed along with the alkyl-substituted 4-methyl-piperidine derivative having general formula (I), in a weight ratio ranging from 0.5:1 to 3:1.

20. An alkyl-substituted 4-methyl-piperidine derivative having the formula:

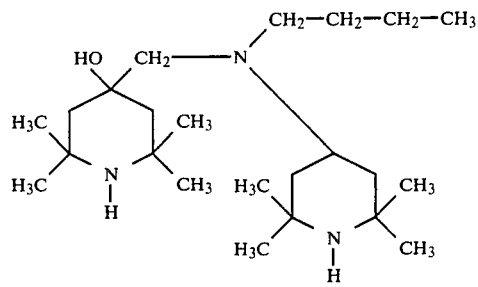

21. A composition comprising a synthetic organic polymer stabilized to light, oxygen and heat by having, incorporated therein, in an amount sufficient to prevent any degrading action of the polymer, the alkyl-substituted 4-methyl-piperidine derivative of claim 20.

22. A composition according to claim 2, in which the alkyl-substituted 4-methyl-piperidine derivative is present in an amount of from 0.1% to 2.0% by weight, extremes included.

23. A composition according to claim 21, in which the synthetic organic polymer is a polyolefin.

24. A composition according to claim 21, in which the synthetic organic polymer is polypropylene consisting prevailingly of isotactic macromolecules.

25. A composition according to claim 21, in which the synthetic polymer is a halogen-containing vinyl polymer.

26. A composition according to claim 21, in which the synthetic polymer is a polyurethane.

27. A composition according to claim 21, in which the synthetic organic polymer is a polymer derived from an α,β-unsaturated acid.

28. The method of stabilizing a synthetic polymer to light, oxygen and heat which comprises, incorporating, in said polymer, the alkyl-substituted 4-methyl-piperidine derivative of claim 20, in an amount sufficient to prevent any degrading action of the polymer.

29. The method of claim 28, in which the alkyl-substituted 4-methyl-piperidine derivative is present in an amount of from 0.1% to 2.0% by weight, extremes included.

30. An alkyl-substituted 4-methyl-piperidine derivative having the formula

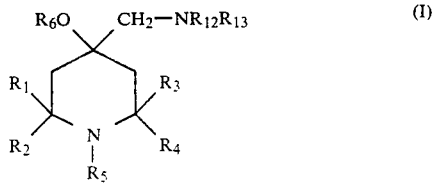

in which
$R_1$, $R_2$, $R_3$ and $R_4$, the same or different, are $C_1$–$C_4$ alkyl or $R_1$ and $R_2$ and/or $R_3$ and $R_4$ together form a cyclo-alkylene radical containing from 3 to 12 carbon atoms;
$R_5$ is hydrogen, $C_1$–$C_4$ alkyl, $C_1$–$C_6$ oxyalkyl or alkoxy; an aryl or aryl-alkyl radical containing from 6 to 18 carbon atoms, an alkenyl radical containing from 2 to 6 carbon atoms, or the group:

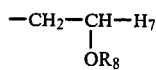   (a)

wherein $R_7$ is hydrogen, $C_1-C_4$ alkyl or $C_1-C_6$ alkoxy, and $R_8$ is hydrogen, $C_1-C_4$ alkyl, or the group:

   (b)

wherein $R_9$ is hydrogen, $C_1-C_{18}$ alkyl, a phenyl or benzyl radical or the group:

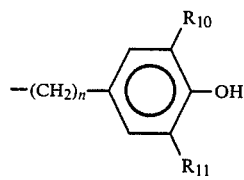   (c)

wherein n is an integer from 1 to 10, and $R_{10}$ and $R_{11}$ are hydrogen or $C_1-C_4$ alkyl;

$R^6$ is hydrogen, an alkyl radical, an alkyl-carbonyl radical in which the alkyl group contains from 1 to 22 carbon atoms, a phenyl-alkyl-carbonyl radical, a cyclo-alkyl-carbonyl radical or a phenyl-carbonyl radical, in which the phenyl or cyclo-alkyl nucleus is optionally substituted by alkyl groups containing from 1 to 3 carbon atoms; and $R_{12}$ and $R_{13}$, the same or different, are $C_1-C_{10}$ alkyl, $C_2-C_{10}$ alkylene or alkynyl;

benzyl, phenyl or the corresponding alkyl-substituted compounds;

the radical:

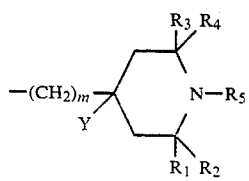   (d)

wherein $R_1, R_2, R_3, R_4$ and $R_5$ have the meaning as in formula I, m is an integer from 0 to 3 and Y is hydrogen, a hydroxyl group, an oxy-alkyl-carbonyl radical, an oxy-phenyl-carbonyl radical, an oxy-cyclo-alkyl-carbonyl radical, in which the phenyl or cyclo-alkyl group may be alkyl-substituted; the radical:

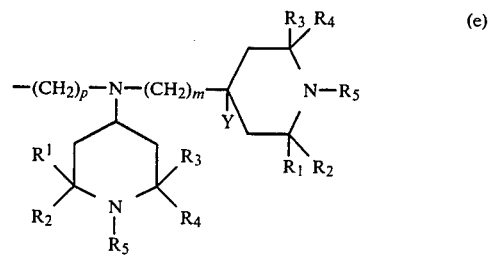   (e)

wherein $R_1, R_2, R_3, R_4, R_5$, m and Y have the same meaning as in formula (d) and p is an integer ranging from 1 to 12;

the radical:

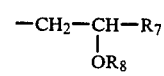   (f)

wherein $R_7$ and $R_8$ have the same meaning as in formula (a);

$R_{12}$ and $R_{13}$ form, along with the nitrogen atom to which they are linked, a simple or alkyl-substituted morpholine or piperidine group;

$R_{12}$ and $R_{13}$ together form the group:

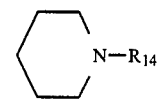   (g)

either simple or alkyl-substituted in the nucleus, in which $R_{14}$ may be hydrogen, an alkyl radical containing from 1 to 6 carbon atoms, or the radical:

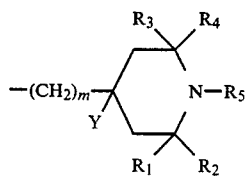   (h)

wherein m, $R_1, R_2, R_3, R_4$, and Y have the meaning as in formula (d);

the triazine radical:

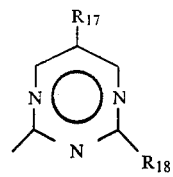   (i)

wherein $R_{17}$ and $R_{18}$, independently of each other, are $C_1-C_{18}$ alkyl, $C_1-C_{18}$ alkoxy or alkyl-oxy, or the radical:

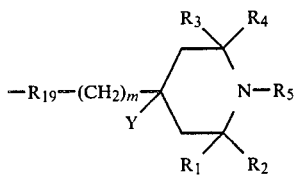 (j)

wherein $R_1$, $R_2$, $R_3$, $R_4$, $R_5$, m and Y have the meanings as in formula (d) and $R_{19}$ is oxygen or $-N-R_{12}$; or $-R_{12}$ or $R_{13}$ is or are hydrogen, except that, when radical (i) is present, $R_{12}$ and $R_{13}$ are not hydrogen.

31. An alkyl-substituted 4-methyl piperidine derivative according to claim 30 in which X is $NR_{12}R_{13}$, $R_{12}$ is a $C_1$–$C_4$ alkyl, and $R_{13}$ has the formula

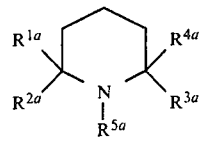

in which $R^{1a}$ to $R^{5a}$ inclusive have the same meanings as $R^1$ to $R^5$ inclusive in formula I.

* * * * *